US009514527B2

United States Patent
Ollivier et al.

(10) Patent No.: US 9,514,527 B2
(45) Date of Patent: Dec. 6, 2016

(54) METHOD AND DEVICE FOR ACQUIRING SEVERAL IMAGES OF THE SAME PACKAGE WITH THE AID OF A SINGLE LINEAR CAMERA

(75) Inventors: Michel Ollivier, Acigne (FR); Jacques Etienne, Laille (FR); Eric Pirot, Cesson-Sevigne (FR); Laurent Roubert, Bourg des Comptes (FR)

(73) Assignee: Bizerba Luceo, Vern-sur-Seiche (FR)

( * ) Notice: Subject to any disclaimer, the term of this patent is extended or adjusted under 35 U.S.C. 154(b) by 362 days.

(21) Appl. No.: 14/131,244

(22) PCT Filed: Jul. 11, 2012

(86) PCT No.: PCT/FR2012/051640
§ 371 (c)(1),
(2), (4) Date: Jan. 7, 2014

(87) PCT Pub. No.: WO2013/007951
PCT Pub. Date: Jan. 17, 2013

(65) Prior Publication Data
US 2014/0146169 A1 May 29, 2014

(30) Foreign Application Priority Data

Jul. 11, 2011 (FR) ...................................... 11 56303

(51) Int. Cl.
*H04N 7/18* (2006.01)
*H04N 9/47* (2006.01)
(Continued)

(52) U.S. Cl.
CPC ............. *G06T 7/0004* (2013.01); *G01N 21/88* (2013.01); *G01N 21/90* (2013.01); *G01N 21/95* (2013.01);
(Continued)

(58) Field of Classification Search
None
See application file for complete search history.

(56) References Cited

U.S. PATENT DOCUMENTS 6,460,770 B1 * 10/2002 Kucharczyk ....... G06K 7/10544
235/462.01
2004/0131256 A1 * 7/2004 Fujieda ................. G06T 7/0006
382/199

(Continued)

FOREIGN PATENT DOCUMENTS

EP 0 926 486 6/1999
EP 1 118 854 7/2001
(Continued)

*Primary Examiner* — Frederick Bailey
*Assistant Examiner* — Talha M Nawaz
(74) *Attorney, Agent, or Firm* — Clark & Brody (57) ABSTRACT

A method of inspecting packages with the help of a linear image sensor comprises the steps of:
    for each movement increment, cyclically acquiring a sequence of n successive image lines (l1, l2, . . . , ln), the n image lines of each sequence being obtained with exposure times (Ti) and/or lighting conditions (Ek) that are different;
    grouping together the image lines (l1, l2, . . . , ln) obtained in the sequences while using both the same exposure times (Ti) and the same lighting conditions (Ek) so as to obtain n' superposable images (I1, I2, . . . , In) of at least j image lines; and
    analyzing the n' superposable images (I1, I2, . . . , In) separately or in combination in order to determine at least one characteristic of the packages. A device for package inspection includes a process and control unit that employs the steps of the method.

16 Claims, 4 Drawing Sheets

(51) Int. Cl.
  *G06T 7/00* (2006.01)
  *G01N 21/88* (2006.01)
  *G01N 21/90* (2006.01)
  *G01N 21/95* (2006.01)
  *B29L 31/00* (2006.01)
  *B29C 65/82* (2006.01)
  *B29C 65/00* (2006.01)

(52) U.S. Cl.
  CPC ............ *H04N 7/18* (2013.01); *B29C 65/8253* (2013.01); *B29C 66/112* (2013.01); *B29C 66/131* (2013.01); *B29C 66/242* (2013.01); *B29C 66/342* (2013.01); *B29C 66/53461* (2013.01); *B29C 66/7373* (2013.01); *B29C 66/849* (2013.01); *B29L 2031/712* (2013.01)

(56) References Cited

U.S. PATENT DOCUMENTS

| 2005/0220332 | A1* | 10/2005 | Akutagawa | G03F 1/84 382/144 |
| 2006/0215899 | A1* | 9/2006 | Oaki | G06T 7/001 382/145 |
| 2006/0244954 | A1* | 11/2006 | Daley | B07C 5/3422 356/237.1 |
| 2007/0084285 | A1* | 4/2007 | De Baerdemaeker | G01M 3/24 73/587 |
| 2007/0098248 | A1* | 5/2007 | Toyoda | G06T 7/001 382/145 |
| 2009/0095047 | A1* | 4/2009 | Patel | G06K 7/10722 73/1.01 |
| 2009/0190139 | A1* | 7/2009 | Fisher | G01B 11/2518 356/613 |
| 2009/0244698 | A1* | 10/2009 | Zust | G02B 21/365 359/368 |
| 2010/0163626 | A1* | 7/2010 | Olmstead | G06K 7/10574 235/462.41 |
| 2012/0067956 | A1* | 3/2012 | Gao | G06K 7/1095 235/455 |
| 2012/0081386 | A1* | 4/2012 | Wiemker | G06T 7/0012 345/589 |
| 2012/0307236 | A1* | 12/2012 | Ortner | G01N 21/9505 356/239.3 |
| 2013/0020392 | A1* | 1/2013 | Olmstead | G06K 7/10722 235/440 |
| 2014/0029019 | A1* | 1/2014 | Leconte | G01B 11/06 356/632 |

FOREIGN PATENT DOCUMENTS

| EP | 1 790 975 | 5/2007 |
| FR | 2 846 425 | 4/2004 |
| FR | 2 907 424 | 4/2008 |
| FR | 2 907 553 | 4/2008 |
| WO | 2010/052431 | 5/2010 |

* cited by examiner

METHOD AND DEVICE FOR ACQUIRING SEVERAL IMAGES OF THE SAME PACKAGE WITH THE AID OF A SINGLE LINEAR CAMERA

The present invention relates to the technical field of optoelectronic inspection of packages of product relating to the agrifood, pharmaceutical, ophthalmic, or cosmetics fields, i.e. perishable products. In this field of application, the invention seeks more particularly to inspect the quality of the seals of the packages, such as for example heat-sealed packages.

In the field of inspecting heat-sealed packages, there is a need to inspect the quality of the seals of the package in order, for example, to detect the presence of bubbles or the presence of inclusions or the presence of foreign bodies.

Thus, by way of example, document WO 2010/052431 discloses causing packages to travel past a linear camera, the packages being illuminated by a light source. The passage of a package past the linear camera enables a series of linear images to be acquired, which images are processed in order to detect defects present in the seals.

That type of inspection gives satisfaction in practice provided it is used for inspecting packages in which the inspection zone including the seals possesses optical characteristics that are substantially identical or uniform. An appropriately selected light source then enables the defects present in the seals of such packages to be detected. Nevertheless, it happens more and more frequently that the light transmission or reflection characteristics of the inspected zones are not uniform. Certain portions of the inspected zones include markings or coloring, while other portions are transparent. The optical characteristics or properties of the material constituting the cell and/or the film may vary locally between being transparent, translucent, diffusing, or opaque, between being reflecting or mat, and in terms of color, brightness, and saturation. For packages of this type, the use of a camera and of a light source does not enable defects to be detected in all portions of the inspected seals.

In an attempt to remedy that drawback, it is known to use two inspection stations having lighting that differs from one station to the other. Each station is adapted to detect the defects that appear in one of the two zones of the package that present different optical characteristics. Separate or combined processing of the images acquired by the two stations makes it possible to inspect the packages throughout the zone for inspection.

That solution is expensive since it requires two inspection stations to be provided. In addition, that solution is relatively complex to implement because the processing needs to be performed on images coming from two stations, which images can be difficult to bring into coincidence.

There is thus a need to be able to have a technique for inspecting packages that is simple and inexpensive to perform, while being designed to enable an inspection zone to be inspected in full even though it presents optical characteristics that are locally not uniform.

To achieve this object, the invention provides a method of inspecting packages, or more particularly of inspecting the quality of seals, with the help of a linear image sensor that delivers successive image lines, each inspected package moving relative to said sensor and being illuminated with the help of at least one lighting system.

According to the invention, the method comprises the following steps:

for each movement increment, cyclically acquiring a sequence of n successive image lines (with n greater than 1), so as to obtain sequences for j movement increments, the n image lines in each sequence being obtained with exposure times and/or lighting conditions that are different;

grouping together the image lines obtained in the sequences using both the same exposure times and the same lighting conditions in such a manner as to obtain n superposable images of at least j image lines, the images being obtained with exposure times and/or lighting conditions that are different; and analyzing the n images separately or in combination in order to determine at least one characteristic of the inspected package(s).

The method of the invention makes it possible to acquire a plurality of images of the same package using a single linear camera.

In addition, the method of the invention may also present in combination at least one and/or another of the following additional characteristics:

the number j of acquired sequences makes it possible to reconstitute n different images of dimension equal to the number j of sequences multiplied by the width of the field of the sensor, this dimension (j×L) being appropriate for covering at least the image of one package, of a set of packages, or of an inspection region forming a portion of a package;

in each sequence of n image lines, at least two image lines are obtained with exposure times that are different so as to obtain two images of dynamic ranges adapted to different lighting conditions and/or to different transmission or reflection characteristics of the package;

in each sequence of n image lines, at least two image lines are obtained under lighting conditions that differ in terms of instantaneous light power, and/or lighting duration, and/or wavelength spectrum, and/or polarization state, and/or position of the lighting system relative to the package, and/or the shape of the light source of the lighting system, and/or the directivity thereof, and/or the diffuse nature thereof, and/or the uniformity thereof;

at least one light source of the lighting system is controlled to illuminate the package solely during a time that is strictly less than the reciprocal of the reading rate of the linear sensor;

at least one light source of the lighting system is controlled to light the package during an exposure time of the linear sensor corresponding to one of the n image lines of each sequence;

for each acquisition of an image line with one exposure time and one light source, the light source is switched on before the beginning of the exposure of the linear image sensor, and then said light source is switched off after the end of the exposure of the linear image sensor;

the inspected packages are caused to move relative to the sensor in translation;

for inspecting packages each made up of at least one cell containing product and hermetically closed by heat-sealing by means of a film, the method comprises the following steps:

moving the inspected packages in translation in a direction that is not parallel to the optical axis of the linear image sensor;

placing the linear image sensor on the same side as the cells or on the same side as the film so that its field of width measured perpendicularly to the travel direction covers one or more cells;

for each sequence, acquiring a first image line with a first exposure time while activating a first light source situated on the same side as the cells, and then a second image line with a second exposure time while activating a second light source situated on the same side as the film;

grouping together the first image lines of each sequence in such a manner as to obtain a first image of dimensions (j×L) for inspecting in light reflected or diffused by the surface of the packages, or diffused by the package; and grouping together the second image lines of each sequence so as to obtain a second image of dimensions (j×L) for inspecting in light transmitted or diffused in the material of the packages;

for a first portion of the package, acquiring sequences, each formed by a first image line and a second image line, and for a second portion of the package, acquiring sequences, each comprising the first image line and a second image line obtained with a third exposure time while activating a third light source situated on the same side as the linear sensor; and determining as a characteristic of the packages, the quality of the sealing.

The invention also provides a device for inspecting packages and more particularly the seals of packages containing product, the packages being caused to move past a linear image sensor that delivers successive image lines, the device including at least one lighting system enabling the packages to be illuminated.

According to the invention, the device comprises:

means for setting the exposure times of the linear image sensor to different values;

means for modifying the lighting conditions of the lighting system to different values; and an image processor and control unit comprising:

means for controlling the means for setting the exposure times, the means for modifying the lighting conditions of the lighting system, and the acquisition of images by the linear image sensor in such a manner as to acquire cyclically a sequence of n successive images (with n greater than 1) for each increment so as to obtain sequences for j movement increments, the n image lines of each sequence being obtained with exposure times and/or lighting conditions that are different;

means for grouping together the image lines obtained in the sequences having both the same exposure times and the same lighting conditions so as to obtain n superposable images of at least j image lines the images being obtained with exposure times and/or lighting conditions that are different; and means for analyzing the n images separately or in combination in order to determine at least one characteristic of the inspected package(s) and in particular seals of said packages.

Furthermore, the device of the invention may also present in combination at least one and/or another of the following additional characteristics:

the lighting system comprises at least one light source with a lighting duration that is shorter than the reading period of the linear image sensor, the duty ratio of the illuminating by the light source possibly reaching 50%;

a device for inspecting packages made up of at least one cell containing product and hermetically closed by heat-sealing by means of a film, the device comprises:

a linear image sensor situated on the same side as the cells or on the same side as the film so that its field of width measured perpendicularly to the travel direction covers one or more cells;

as the inspecting system, a first light source situated on the same side as the cells and illuminating the package over at least the field of the linear image sensor, and a second light source situated on the same side as the film; and a processor and control unit acting:

for taking the first image lines of the sequences, to exposure the sensor for a first exposure time and activating the first light source during said first exposure time; and for taking the second image lines of the sequences, to expose the sensor during a second exposure time and activating the second light source during said second exposure time; and the lighting system includes a third light source situated on the same side as the linear image sensor and illuminating the package over at least the field of the linear sensor, the processor and control unit acts:

for a first portion of the package, to acquire sequences each made up of the first image line obtained with the first light source and the second image line obtained with the second light source; and for a second portion of the package, to acquire sequences each formed by the first light image obtained with the first light source and the second light image obtained with the third light source, with an exposure time of the linear image sensor.

The device of the invention may also present the following characteristics:

in order to inspect packages made up of at least one cell containing product and hermetically closed by heat-sealing by means of a film, the device comprises:

a linear image sensor situated on the same side as the cells or on the same side as the film so that its field of width measured perpendicularly to the travel direction covers one or more cells;

as the lighting system, a light source situated on the side relative to the moving packages opposite from the side on which the camera is situated and illuminating the package over at least the field of the linear image sensor; and a processor and control unit acting:

for the first image lines of the sequences, to expose the sensor for a first exposure time while activating the light source during said exposure time; and for taking the second image lines of the sequences, to expose the sensor during a second exposure time and activating the light source during said exposure time.

Various other characteristics appear from the following description made with reference to the accompanying drawings, which show embodiments of the invention as non-limiting examples.

The invention relates to a method of inspecting a package 1 made of a material that enables inspection to be performed by taking images and that contains a perishable product. The method of the invention seeks more particularly to verify the quality of seals presented by such packages. In a non-exclusive but advantageous variant implementation, the package 1 is made completely or in part out of materials that are translucent or transparent. By way of example, the package 1 may contain a product relating for example to the agrifood, pharmaceutical, ophthalmic, or cosmetic fields.

Figure 1:
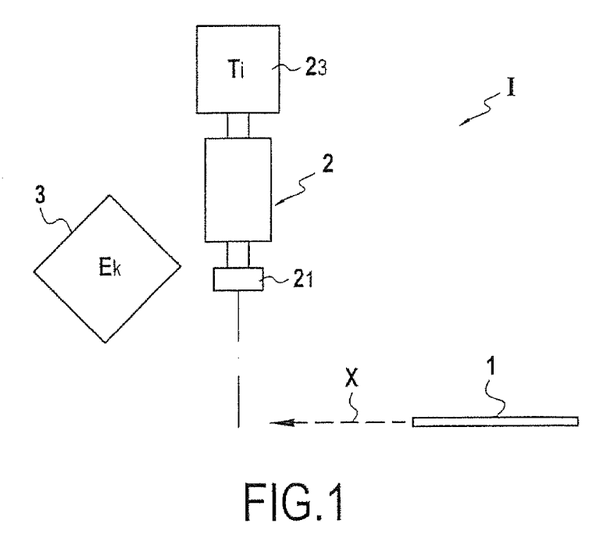
FIG. 1 is a diagrammatic elevation view of an embodiment of a device for explaining the general principle of the inspection method in accordance with the invention.
Figure 2:
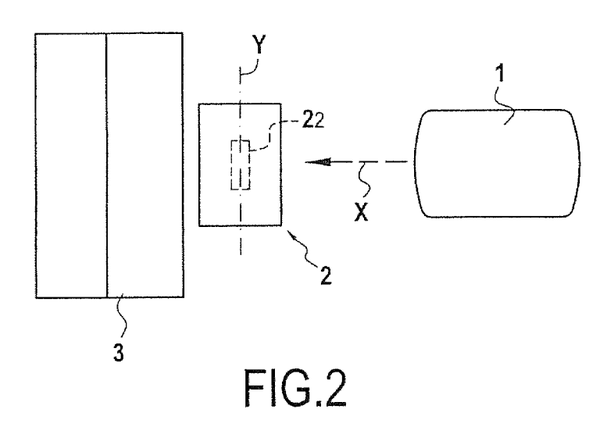
FIG. 2 is a plan view of the device shown in FIG. 1.

FIGS. 1 and 2 are diagrams showing an example of a device I for performing the inspection method in accordance with the invention. The device I has a linear image sensor 2 and a lighting system 3 for illuminating the package 1. The linear image sensor 2, such as a linear camera, comprises a lens $2_1$ and a strip $2_2$ of photocells extending along a direction Y. The linear image sensor 2 has a field width L. The linear image sensor 2 delivers successive image lines, and it is connected to an image processor and control unit $2_3$.

In accordance with the invention, the linear image sensor 2 includes a system enabling its exposure to light to be adjusted. In a preferred variant implementation, provision is made to use a linear camera with an adjustable integration time enabling its exposure to be adjusted. The integration time or exposure time is the duration during which the sensitive surface of the linear camera is exposed to light prior to transferring its electric charges. Naturally, it is possible to envisage adjusting the exposure time of the linear image sensor 2 in some other way, e.g. by a controlled mechanical or electronic shutter.

The device I also has a system that is not shown for ensuring that the package 1 moves relative to the linear sensor 2 and to the lighting system 3 in order to enable the package 1 to be inspected over an inspection zone that is greater than the field of the linear sensor 2. Thus, the zone inspected by the linear image sensor 2 covers all or only part of one or more packages 1. In the example shown in FIGS. 1 and 2, the package 1 is moved in translation along a travel direction X. Naturally, the method of the invention may present movement in rotation optionally combined with movement in translation. Likewise, in the example shown, the package 1 is moved relative to the linear image sensor 2 and to the lighting system 3. Naturally, the method of the invention also applies to a package 1 remaining stationary while the linear sensor 2 and the lighting system 3 are mounted to move relative to the package 1. In any event, movement of the package relative to the camera enables regions of the inspected package to be scanned.

For each movement increment, and specifically for each step of movement in translation of the package 1, the method of inspection of the invention consists in acquiring a sequence of n successive image lines taken by the linear image sensor 2 under lighting conditions that are different and/or with exposure times for the linear sensor 2 that are different.

Figure 3:
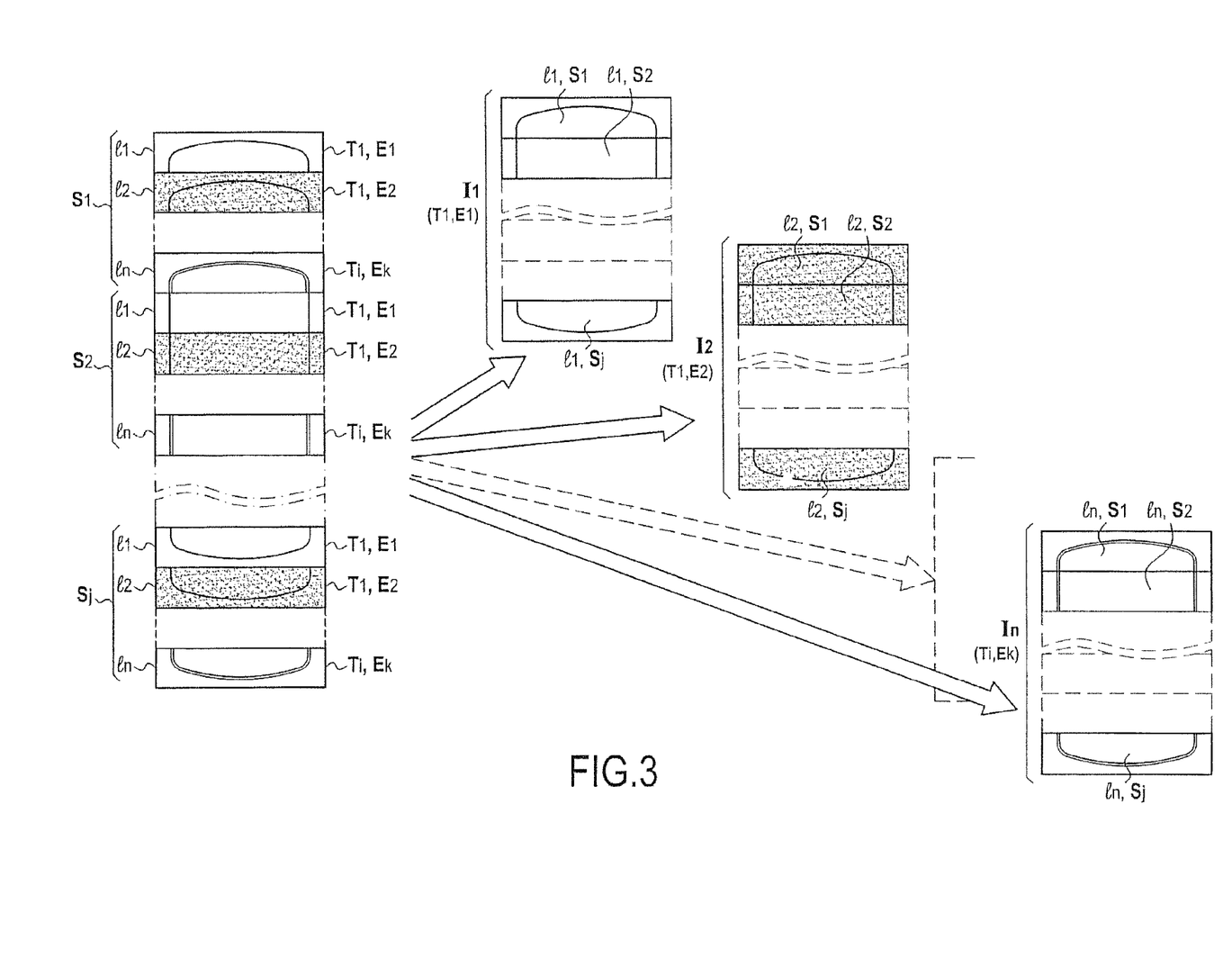
FIG. 3 shows the principle of the inspection method in accordance with the invention.

Thus, and as can be seen more clearly in FIG. 3, for each movement increment, the linear image sensor 2 acquires a sequence, i.e. for j movement increments, it acquires a number j of successive sequences S1, S2, . . . , Sj. In each successive sequence S1, S2, . . . , Sj, the linear image sensor 2 acquires n image lines l1, l2, . . . , ln of the corresponding inspection zone of the package 1 (where n is strictly greater than 1). Within each sequence, each image line l1, l2, . . . , ln of the sequence is acquired either using an exposure time Ti that is different from the exposure times of the other image lines, or under lighting conditions Ek that are different from the lighting conditions of the other image lines, or indeed with an exposure time Ti that is different from the other image lines and under lighting conditions Ek that are different from the other image lines.

It can be seen from the above that the lighting system 3 is controlled so as to deliver lighting conditions Ek that can be modified for at least some of the image lines taken during a sequence. Thus, the lighting system 3 makes it possible to obtain lighting conditions that differ, for example, in terms of instantaneous light power and/or lighting duration and/or wavelength spectrum and/or polarization state and/or position of the lighting system relative to the package and/or the shape of the light source of the lighting system and/or the directivity thereof and/or the diffuse nature thereof and/or the uniformity thereof.

The lighting system 3 may thus comprise one or more light sources with different lighting characteristics and/or different positions relative to the package 1 and/or different shapes (rectangular, elongate, etc.) and/or different dimensions. In a variant implementation, at least one light source of the lighting system 3 is controlled to light the package 1 only for a time that is strictly less than the reciprocal of the reading rate of the linear sensor 2. In another variant implementation, at least one light source of the lighting system 3 is controlled to light the package 1 only during an exposure time of the linear sensor 2 that corresponds to one of the n image lines l1, l2, . . . , ln of each sequence.

According to another advantageous implementation characteristic, for each acquisition of an image line with an exposure time Ti and a light source, the method consists in switching on the light source before the beginning of the exposure of the linear image sensor, and in switching off said light source after the end of the exposure of the linear image sensor.

In a variant implementation, for each acquisition of an image line with an exposure time Ti and a light source, the method consists in switching on the light source after the beginning of the exposure of the linear image sensor, and in switching off said light source before the end of the exposure of the linear image sensor.

Naturally, the lighting conditions Ek may remain identical for at least some of the image lines taken. Under such circumstances, the exposure time Ti of the linear sensor 2 varies at least for such image lines that have lighting conditions Ek that are identical.

Thus, the processor and control unit $2_3$ serves to adjust the exposure times Ti of the linear sensor 2 in such a manner as to obtain at least two image lines with different exposure times Ti. At least two images may thus be obtained with dynamic ranges that match different lighting conditions and/or locally different transmission or reflection characteristics of the package. In an advantageous implementation, the exposure times Ti of two successive lines are different.

In the example shown in FIG. 3, for a movement increment of the package 1, the sequence S1 comprises in succession: a first image line l1 taken with a first exposure time T1 and under first lighting conditions E1; a second image line l2 taken with the first exposure time T1 and under second lighting conditions E2 different from the first lighting conditions E1; and successive image lines up to a last image line ln taken with respective exposure times Ti and lighting conditions Ek. The sequence S1 thus comprises a succession of n image lines l1, l2, . . . , ln.

For a following movement increment, the method acquires in succession to the first sequence S1, a second sequence S2 of n successive image lines l1, l2, . . . , ln. Each of the image lines l1, l2, . . . , ln of this second sequence S2 is obtained with respective exposure times and lighting conditions that are identical to those that apply to the first sequence S1. Thus, for the second sequence S2, the first image line l1 is obtained with the first exposure time T1 and the first lighting conditions E1, while the second image l2 is obtained with the first exposure time T1 and the second lighting conditions E2, and so on for all of the other image lines of the second sequence S2.

In the example shown, the image lines of the second sequence S2 are taken using a cycle that is identical to the cycle of image lines taken in the sequence S1. It should be observed that it would also be possible to select an image line cycle that differs from one sequence to the next.

Thus, the method seeks to acquire a sequence cyclically for each movement increment, i.e. for j movement increments it seeks to acquire a number j of sequences S1, S2, . . . , Sj, each sequence S1, S2, . . . , Sj comprising n successive image lines l1, l2, . . . , ln. It should be observed that the number j of sequences S1, S2, . . . , Sj is selected so as to make it possible to take linear images covering all of the selected inspection zone.

The method of the invention then consists in grouping together the image lines l1, l2, . . . , ln obtained during the various sequences S1, S2, . . . , Sj having both the same respective exposure times Ti and the same respective lighting conditions Ek so as to obtain n superposable images I1, I2, . . . , In.

Thus each image I1, I2, . . . , In has j image lines obtained for each of the images with the same exposure time Ti and the same lighting conditions Ek. Thus, the image I1 is obtained by grouping together the first image lines l1 coming from the various sequences S1, S2, . . . , Sj. Likewise, the second image I2 is obtained by grouping together the second image lines l2 obtained in the various sequences S1, S2, . . . , Sj. In general, an image In is made by grouping together the $n^{th}$ image lines obtained in the various sequences S1, S2, . . . , Sj. The order in which the image lines are grouped together in each image is identical for all the reconstituted images when the image line cycles are identical in the sequences S1, S2, . . . , Sj.

Thus, the images I1, I2, . . . , In present a dimension D equal to the number j of sequences S1, S2, . . . , Sj multiplied by the field width L of the linear image sensor 2. This dimension D, which is expressed as a number of pixels (D=L×j), is chosen to cover at least the inspection zone of the package.

It should be considered that the n images I1, I2, . . . , In present the characteristic of being superposable in the sense that each pixel taken in an image possesses coordinates that are identical to the corresponding pixels taken in the other images. Such image superposition is obtained on each movement increment by making a series of image lines in which the same zone of the package appears. Although the relative movement is generally continuous, the rate at which image lines are acquired is sufficiently high for it to be possible to consider that all of the image lines l1, l2, . . . , ln in a sequence are all images of a single strip or zone of the package 1. Naturally, the speed at which the image lines are acquired and the number of image lines taken are selected as a function of the speed at which the package moves and of the resolution of the images so as to obtain images that present the characteristic of being superposable. It should be considered that the n images l1, l2, . . . , ln have the characteristic of being superposable in the sense that their spatial resolution is the same. Such image superposition is obtained for each movement increment by taking a series of image lines at a repeatable rate.

Furthermore, it should be observed that the reconstituted images I1, I2, . . . , In present different exposure times Ti among the images and/or different lighting conditions Ek likewise among the images. The exposure times Ti of the linear sensor 2 and the lighting conditions Ek of the package 1 are selected as a function of the characteristics that are to be determined of the package, where revealing those characteristics depends in particular on the light transmission and reflection of the package. Taking images with different exposure times Ti and/or under different lighting conditions Ek enables a single linear image sensor 2 to detect various specific characteristics of the package with uniform and optimum inspection accuracy even when the package presents optical characteristics or properties of the materials of the cell and/or the film that vary locally between being transparent, translucent, diffusing, or opaque, between being glossy or mat, and in terms of color, brightness, and saturation.

The method of the invention then consists in analyzing the n images I1, I2, . . . , In separately or in combination in order to determine at least one characteristic of the packages for inspection. A comparative analysis of the images I1, I2, . . . , In is made that much easier when such images are superposable. The characteristics deduced from the analysis may, for example, be defects, that are revealed in one and/or another of the images taken.

The method of the invention is performed by the device I for inspecting packages 1. For this purpose, the device I comprises:

adjustment means for setting the exposure time Ti of the linear image sensor 2 so as to obtain image lines with exposure times Ti that differ between lines, these adjustment means being internal or external to the sensor 2; and adjustment means for modifying the lighting conditions Ek of the lighting system 3 in order to obtain image lines with lighting conditions that are different between lines, these adjustment means being internal or external to the lighting system 3.

The inspection device 1 also has an image processor and control unit $2_3$ comprising:

means for controlling the adjustment means for setting the exposure times, the adjustment means for modifying the lighting conditions of the lighting system 3, and the acquisition of images by the linear image sensor in such a manner as to acquire a sequence of n successive image lines l1, l2, . . . , ln (for n greater than 1) cyclically on each movement increment so as to obtain sequences S1, S2, . . . , Sj for j movement increments, the n image lines of each sequence being obtained with exposure times Ti and/or lighting conditions Ek that are different;

means for grouping together the image lines l1, l2, . . . , ln obtained in the sequences that have both the same exposure times Ti and the same lighting conditions Ek so as to obtain n superposable images I1, I2, . . . , In of at least j image lines, the images being obtained with exposure times Ti and/or lighting conditions Ek that are different; and means for analyzing the n images I1, I2, . . . , In separately or in combination in order to determine at least one characteristic of the inspected package(s).

According to an advantageous characteristic, the lighting system 3 has at least one light source presenting a lighting duration that is shorter than the reading period of the linear image sensor 2, the duty ratio of the lighting from the light source possibly reaching 50%. Typically, for a linear image sensor operating at 10 kilohertz (kHz), the order of magnitude of the duration of lighting is less than 100 microseconds (µs).

Figure 4A:
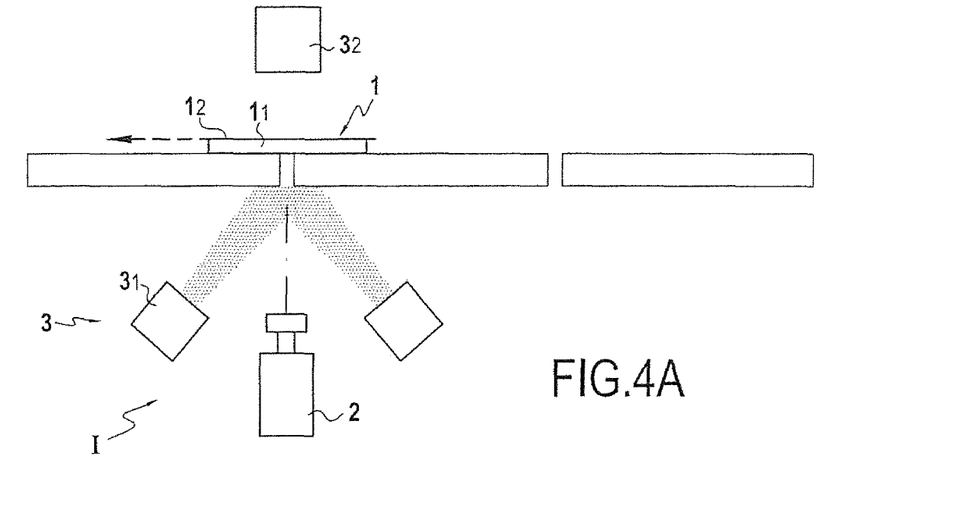
FIGS. 4A and 4B show the method in accordance with the invention being applied to inspecting heat-sealed packages, by way of example.
Figure 4B:
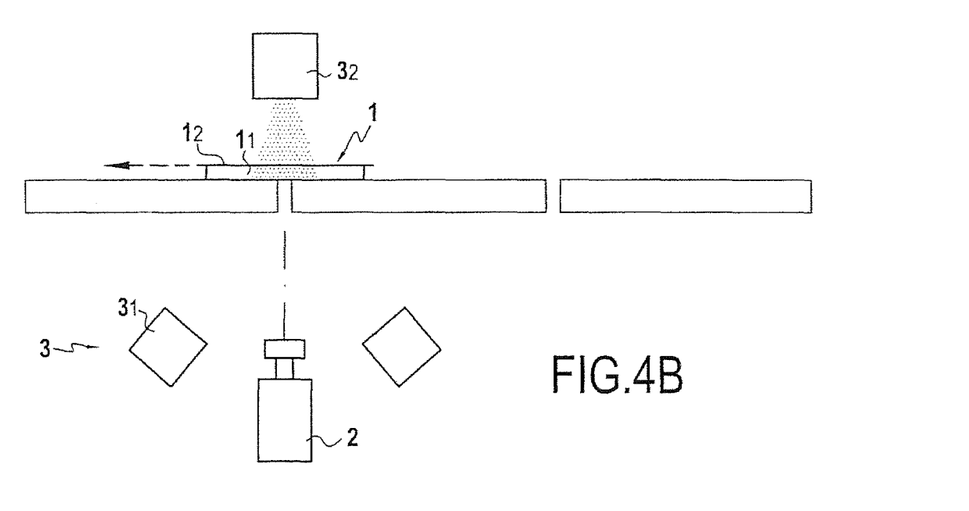

FIGS. 4A and 4B show an example of the method of the invention being applied to inspecting packages 1, each made up of at least one product cell $1_1$ that is hermetically closed by heat-sealing using a film $1_2$. As can be seen from these figures, the package 1 or tray generally comprises a rim running peripherally around each cell $1_1$ and having a closure film $1_2$ heat-sealed thereto. The seals of the packages 1 are inspected with an optical inspection device I performing the method in accordance with the invention. It should be observed that the film $1_2$ may be opaque at least locally, and it may be fastened to a tray that presents the characteristic of being transparent or translucent. Likewise, the film $1_1$ may be transparent or translucent, and it may be fastened on a tray that presents locally the characteristic of being opaque or transparent or translucent.

The packages 1 are caused by any suitable means to move in translation past a linear image sensor 2 in a direction that is not parallel to the optical axis of the linear sensor 2. In the example shown, the packages 1 are moved with the side containing the cells $1_1$ facing towards the linear sensor 2. In other words, the linear sensor 2 is placed under the packages so as to inspect the package on the cell side. Naturally, the linear image sensor 2 is placed in such a manner that its field of width L measured perpendicularly to the travel direction covers the cell of the package for inspecting the seals of the film. If the package has a plurality of cells, then the field of the linear sensor covers all of the cells.

The inspection station I has a lighting system 3 made up of a first light source $3_1$ situated on the same side as the cells $1_1$, i.e. under the packages 1, and a second light source $3_2$ situated on the same side as the film $1_2$, i.e. above the packages 1.

Figure 4C:
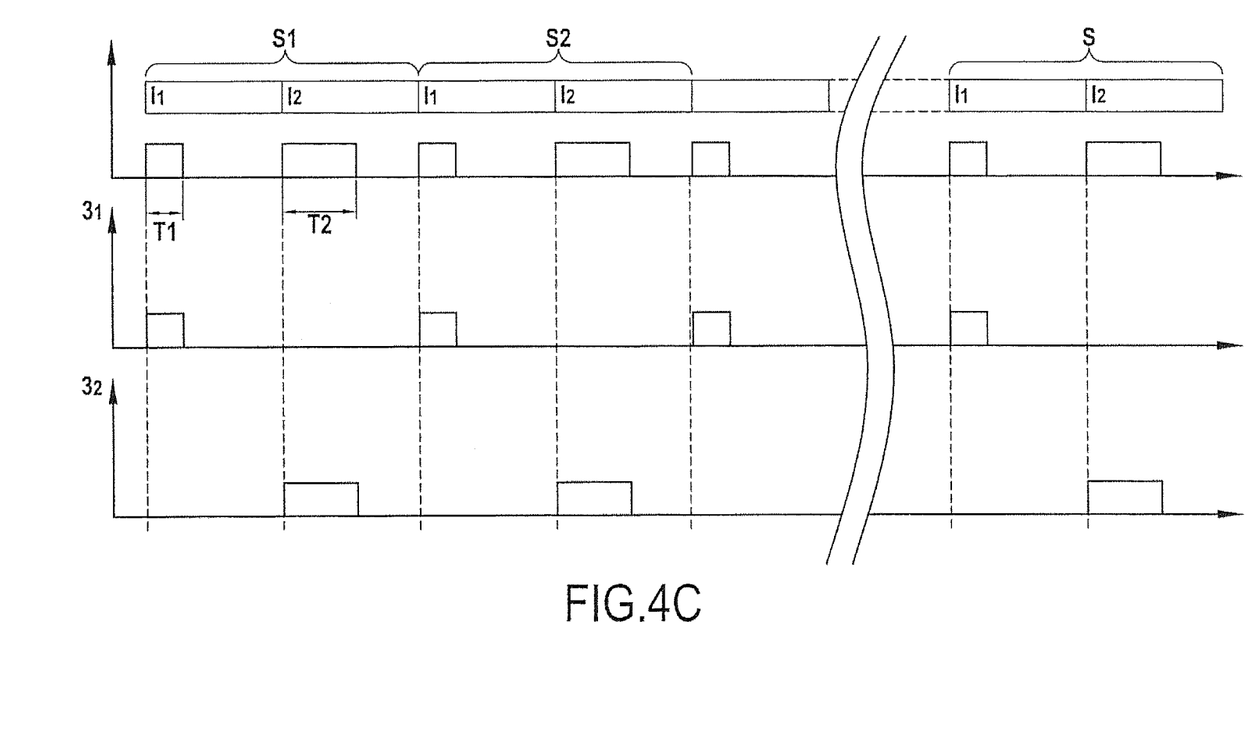
FIG. 4C is a timing chart showing the conditions under which the image lines are obtained.

In accordance with the above-described inspection method, such packages 1 are inspected by using the linear sensor 2 in a first sequence and for a single movement increment to acquire:
  a first image line with a first exposure time T1 for the linear sensor 2 with the package 1 illuminated solely using the first light source $3_1$ (FIGS. 4A, 4C); and
  a second image line with a second exposure time T2 for the linear sensor 2, often different from the first exposure time, while the package 1 is illuminated solely with the second light source $3_2$ (FIGS. 4B, 4C).

For each successive movement increment, the method consists in acting cyclically to acquire a sequence made up of said first image line and said second image line.

Thereafter, the method consists in grouping together the first image lines of each of the sequences as obtained with the first exposure time and the first light source $3_1$ so as to reconstitute an image of dimension given by j×L. This inspection in light reflected or diffused by the surface of the packages serves to detect defects under such reflection conditions.

The method also consists in grouping together the second image lines of each of the sequences obtained with the second exposure time and the second light source $3_2$ in order to reconstitute an image of dimension given by j×L. This inspection using light transmitted or diffused through the package makes it possible to detect defects for such transmission conditions.

Such a method makes it possible to use a single linear image sensor to inspect packages presenting optical characteristics that are locally different. Analyzing the reconstituted images separately or in combination provides inspection that is robust. In particular, the method of the invention makes it possible to determine the quality of the sealing of the packages.

Naturally, it is possible to envisage acquiring a greater number of image lines for each sequence. Likewise, it may be advantageous to acquire different image line sequences for different portions of the package that present optical characteristics that are mutually different. Thus, for a first portion of the package, the method seeks to acquire, for each sequence, the first and second image lines as described above. For a second portion of the package, the method seeks to acquire, for each sequence, the first image line and the second image line as obtained with a third exposure time for the linear image sensor 2 and with a third light source situated beside the linear image sensor 2 and presenting lighting conditions that are different from the second light source $3_2$.

In the example shown, the linear image sensor 2 is arranged on the same side as the cells $1_1$, however it is clear that the linear image sensor 2 could be arranged on the same side as the film $1_2$.

In the example shown in FIGS. 4A and 4B, the inspection station has two light sources $3_1$ and $3_2$. It should be observed that it is possible to envisage an inspection station I having a single light source for inspecting packages each having at least one cell containing product and hermetically closed by heat-sealing using a film. In this variant implementation, the inspection device comprises:
  a linear image sensor situated on the same side as the cells or on the same side as the film so that its field of width measured perpendicularly to the travel direction covers one or more cells;
  a single light source situated on the side relative to the moving packages opposite from the side on which the camera is situated and illuminating the package over at least the field of the linear image sensor; and
  a processor and control unit acting:
    for the first image lines of the sequences, to expose the sensor for a first exposure time while activating the light source during said exposure time; and
    for taking the second image lines of the sequences, to expose the sensor during a second exposure time and activating the light source during said exposure time.

The invention is not limited to the examples described and shown since various modifications can be made thereto without going beyond its ambit.

The invention claimed is:

1. A method of inspecting packages (1) of product with the help of a linear image sensor (2) delivering successive image lines, each inspected package moving relative to said sensor and being illuminated with the help of at least one lighting system (3), the method being characterized by the following steps:
  for each movement increment, cyclically acquiring a sequence of n successive image lines (l1, l2, . . . , ln) (with n greater than 1), so as to obtain sequences (S1, S2, . . . , Sj) for j movement increments, the n image lines in each sequence being obtained with exposure times (Ti) and/or lighting conditions (Ek), in terms of instantaneous light power and/or lighting duration, that are different, wherein in each sequence (S1, S2, . . . , Sj) of n image lines (l1, l2, . . . , ln), at least two image lines are obtained with exposure times (Ti) and/or lighting conditions (Ek), in terms of instantaneous light power and/or lighting duration, that are different so as to obtain two images of dynamic ranges adapted to different lighting conditions and/or to different transmission or reflection characteristics of the package;

grouping together the image lines (l1, l2, . . . , ln) obtained in the sequences using both the same exposure times (Ti) and the same lighting conditions (Ek), in terms of instantaneous light power and/or lighting duration, in such a manner as to obtain n' superposable images (I1, I2, . . . , In) of at least j image lines, the images being obtained with exposure times (Ti) and/or lighting conditions (Ek) that are different; and analyzing the n' superposable images (I1, I2, . . . , In) separately or in combination in order to determine at least one characteristic of the inspected package(s).

2. A method according to claim 1, characterized in that the number j of acquired sequences (S1, S2, . . . , Sj) makes it possible to reconstitute n' different superposable images of dimension (D) equal to the number j of sequences multiplied by the width (L) of the field of the sensor, this dimension being appropriate for covering at least the image of one package, of a set of packages, or of an inspection region forming a portion of a package.

3. A method according to claim 1, characterized in that at least one light source of the lighting system (3) is controlled to light the package (1) solely during a time that is strictly less than the reciprocal of the reading rate of the linear sensor (2).

4. A method according to claim 1, characterized in that at least one light source of the lighting system (3) is controlled to light the package (1) during an exposure time of the linear sensor corresponding to one of the n image lines (l1, l2, . . . , ln) of each sequence (S1, S2, . . . , Sj).

5. A method according to claim 1, characterized in that it consists, for each acquisition of an image line with one exposure time and one light source, in switching on the light source before the beginning of the exposure of the linear image sensor, and in switching off said light source after the end of the exposure of the linear image sensor.

6. A method according to claim 1, characterized in that it consists in causing the inspected packages to move relative to the sensor in translation.

7. A method according to claim 1, characterized in that it consists in determining as a characteristic of the packages, a quality of the sealing.

8. A method for inspecting packages (1) of product with help of a linear image sensor (2) delivering successive image lines, each inspected package moving relative to said sensor and being illuminated with help of at least one lighting system (3), each package being each made up of at least one cell containing product and hermetically closed by heat-sealing by means of a film ($1_2$), the method being characterized by the following steps:

moving the inspected packages in translation in a direction that is not parallel to the optical axis of the linear image sensor (2);

placing the linear image sensor (2) on the same side as the cells or on the same side as the film so that its field of width (L) measured perpendicularly to the travel direction covers one or more cells;

for each movement increment, cyclically acquiring a sequence of n successive image lines (l1, l2, . . . , ln) (with n greater than 1), so as to obtain sequences (S1, S2, . . . , Sj) for j movement increments, the n image lines in each sequence being obtained with exposure times (Ti) and/or lighting conditions (Ek) that are different;

for each sequence, acquiring a first image line with a first exposure time while activating a first light source ($3_1$) situated on the same side as the cells ($1_1$), and then a second image line with a second exposure time while activating a second light source ($3_2$) situated on the same side as the film;

grouping together the first image lines of each sequence in such a manner as to obtain a first image of dimensions (j×L) for inspecting in light reflected or diffused by the surface of the packages, or diffused by the package; and grouping together the second image lines of each sequence so as to obtain a second image of dimensions (j×L) for inspecting in light transmitted or diffused in the material of the packages.

9. A method according to claim 8, characterized in that in each sequence (S1, S2, . . . , Sj) of n image lines (l1, l2, . . . , ln), at least two image lines are obtained under lighting conditions (Ek) that differ in terms of instantaneous light power, and/or lighting duration, and/or wavelength spectrum, and/or polarization state, and/or position of the lighting system relative to the package, and/or the shape of the light source of the lighting system, and/or the directivity thereof, and/or the diffuse nature thereof, and/or the uniformity thereof.

10. A method according to claim 8, characterized in that it consists, for a first portion of the package, in acquiring the sequences each formed by a first image line and a second image line, and in that it consists, for a second portion of the package, in acquiring sequences each comprising the first image line and a second image line obtained with a third exposure time while activating a third light source situated on the same side as the linear sensor.

11. A method according to claim 8, characterized in that it consists in determining as a characteristic of the packages, the quality of the sealing.

12. A device for inspecting packages (1) containing product and hermetically closed by heat-sealing, the packages being caused to move past a linear image sensor (2) that delivers successive image lines, the device comprising at least one lighting system (3) for illuminating the packages and being characterized in that it comprises:

an image processor and control unit ($2_3$)

for modifying the lighting conditions of the lighting system (3), and for the acquisition of images by the linear image sensor in such a manner as to acquire cyclically a sequence of n successive images lines (l1, l2, . . . , ln) (with n greater than 1) for each increment so as to obtain sequences (S1, S2, . . . , Sj) for j movement increments, the n image lines of each sequence being obtained with exposure times (Ti) and/or lighting conditions (Ek), in terms of instantaneous light power and/or lighting duration, that are different;

and for grouping together the image lines (l1, l2, . . . , ln) obtained in the sequences having both the same exposure times (Ti) and the same lighting conditions (Ek), in terms of instantaneous light power and/or lighting duration, so as to obtain n' superposable images (I1, I2, . . . , In) of at least j image lines, the superposable images being obtained with exposure times (Ti) and/or lighting conditions (Ek), in terms of instantaneous light power and/or lighting duration, that are different; and and for analyzing the n' superposable images (I1, I2, . . . , In) separately or in combination in order to determine at least one characteristic of the inspected package(s).

13. A device according to claim 12, characterized in that the lighting system (3) comprises at least one light source with a lighting duration that is shorter than the reading period of the linear image sensor (2), the duty ratio of the illuminating by the light source possibly reaching 50%.

14. A device for inspecting packages (1) containing product and hermetically closed by heat-sealing, the packages being caused to move past a linear image sensor (2) that delivers successive image lines, the device comprising at least one lighting system (3) for illuminating the packages, characterized in that, for inspecting packages (1) made up of at least one cell ($1_1$) containing product and hermetically closed by heat-sealing by means of a film ($1_2$), the device comprises:

- a linear image sensor (2) situated on the same side as the cells or on the same side as the film so that its field of width (L) measured perpendicularly to the travel direction covers one or more cells;
- as the lighting system (3), a first light source ($3_1$) situated on the same side as the cells ($1_1$) and illuminating the package over at least the field of the linear image sensor (2), and a second light source ($3_2$) situated on the same side as the film ($1_2$); and
- a processor and control unit ($2_3$) acting:
  for acquiring cyclically a sequence of n successive image lines (l1, l2, . . . , ln) (with n greater than 1) for each increment so as to obtain sequences (S1, S2, . . . , Sj) for j movement increments, the n image lines of each sequence being obtained with exposure times (Ti) and/or lighting conditions (Ek) that are different;
  for taking first image lines of the sequences, by exposing the sensor (2) for an exposure time (T1) and activating the first light source ($3_1$) during said exposure time (T1); and
  for taking second image lines of the sequences, by exposing the sensor (2) during an exposure time (T2) and activating the second light source ($3_2$) during said exposure time (T2); and
  grouping together the image lines (l1, l2, . . . , ln) obtained in the sequences having both the same exposure times (Ti) and the same lighting conditions (Ek) so as to obtain n' superposable images (I1, I2, . . . , In) of at least j image lines, the superposable images being obtained with exposure times (Ti) and/or lighting conditions (Ek) that are different.

15. A device according to claim 14, characterized in that the lighting system (3) includes a third light source situated on the same side as the linear image sensor (2) and illuminating the package over at least the field of the linear sensor (2), and in that the processor and control unit ($2_3$) acts:

- for a first portion of the package, to acquire sequences each made up of the first image line obtained with the first light source and the second image line obtained with the second light source; and
- for a second portion of the package, to acquire sequences each formed by the first light image obtained with the first light source and the second light image obtained with the third light source, with an exposure time (T3) of the linear image sensor (2).

16. A device for inspecting packages (1) containing product and hermetically closed by heat-sealing, the packages being caused to move past a linear image sensor (2) that delivers successive image lines, the device comprising at least one lighting system (3) for illuminating the packages, characterized in that, in order to inspect packages made up of at least one cell containing product and hermetically closed by heat-sealing by means of a film, the device comprises:

- a linear image sensor situated on the same side as the cells or on the same side as the film so that its field of width measured perpendicularly to the travel direction covers one or more cells;
- as the lighting system, a light source situated on the side relative to the moving packages opposite from the side on which the camera is situated and illuminating the package over at least the field of the linear image sensor; and
- a processor and control unit acting:
  for acquiring cyclically a sequence of n successive image lines (l1, l2, . . . , ln) (with n greater than 1) for each increment so as to obtain sequences (S1, S2, . . . , Sj) for j movement increments, the n image lines of each sequence being obtained with exposure times (Ti) and/or lighting conditions (Ek) that are different;
  for taking first image lines of the sequences, by exposing the sensor for a first exposure time while activating the light source during said exposure time; and
  for taking second image lines of the sequences, by exposing the sensor during a second exposure time and activating the light source during said exposure time;
  for grouping together the image lines (l1, ,l2, . . . , ln) obtained in the sequences having both the same exposure times (Ti) and the same lighting conditions (Ek) so as to obtain n' superposable images (I1, I2, . . . , In) of at least j image lines, the different superposable images being obtained with exposure times (Ti) and/or lighting conditions (Ek) that are different.

* * * * *